United States Patent [19]
Oetliker et al.

[11] Patent Number: 5,127,729
[45] Date of Patent: Jul. 7, 1992

[54] METHOD AND APPARATUS FOR GUIDING AND COLLECTING LIGHT IN PHOTOMETRY OR THE LIKE

[75] Inventors: Hans Oetliker, Muri; Peter Winiger, Wohlen; Sonia Stempeel, Zurich, all of Switzerland

[73] Assignee: Inotech AG, Wohlen, Switzerland

[21] Appl. No.: 919,257

[22] Filed: Oct. 15, 1986

Related U.S. Application Data

[63] Continuation of Ser. No. 731,868, May 8, 1985, abandoned, which is a continuation-in-part of Ser. No. 684,482, Dec. 21, 1984, abandoned.

[30] Foreign Application Priority Data

Dec. 24, 1983 [DE] Fed. Rep. of Germany ....... 3347080

[51] Int. Cl.$^5$ ...................... G01N 21/47; G01N 21/64
[52] U.S. Cl. ...................... 356/317; 356/73; 356/338; 250/458.1
[58] Field of Search ................ 356/317, 318, 73, 338; 250/458.1, 459.1, 461.1, 461.2

[56] References Cited

U.S. PATENT DOCUMENTS

| | | | |
|---|---|---|---|
| 3,946,239 | 3/1976 | Salzman et al. | 250/461.2 |
| 4,124,302 | 11/1978 | Kuzmin | 356/440 |
| 4,188,542 | 2/1980 | Hogg et al. | 250/458.1 |
| 4,188,543 | 2/1980 | Brunsting et al. | 250/458.1 |
| 4,189,236 | 2/1980 | Hogg et al. | 250/461.2 X |
| 4,200,802 | 4/1980 | Salzman et al. | 356/318 X |
| 4,245,910 | 1/1981 | Källander | 356/338 |
| 4,341,993 | 7/1982 | Brunsting et al. | 250/458.1 X |

FOREIGN PATENT DOCUMENTS

| | | | |
|---|---|---|---|
| 91126 | 10/1983 | European Pat. Off. | 356/318 |
| 8202950 | 9/1982 | PCT Int'l Appl. | 356/437 |

Primary Examiner—F. L. Evans
Attorney, Agent, or Firm—Bachman & LaPointe

[57] ABSTRACT

A method and an apparatus for guiding and collecting light which issues from a light source and which is passed in the form of an incident primary beam to a specimen or like material to be measured are intended to optimize guiding and collecting the light. That aim is achieved by a method wherein the material to be measured is disposed at a focus of a reflection surface formed at least as half an ellipsoid of revolution, and beams leaving said material are reflected at the reflection surface. In that connection, the primary beam is emitted directly in the center of the material to be measured. An apparatus of the kind set forth above is characterized in that at least the material (14) to be measured is surrounded by a reflection surface in the form at least of a half ellipsoid of revolution (13) and the material (14) to be measured is disposed at the focus (F1) thereof. In another apparatus, the measuring chamber (12) is defined by a reflection surface in the form of an ellipsoid (13) of revolution, the light source (3) being disposed at one focus thereof and the material to be measured being disposed at the other focus.

3 Claims, 6 Drawing Sheets

METHOD AND APPARATUS FOR GUIDING AND COLLECTING LIGHT IN PHOTOMETRY OR THE LIKE

The instant application is a continuation of U.S. patent application Ser. No. 731,868, filed May 8, 1985, now abandoned, which in turn is a continuation-in-part of U.S. patent application Ser. No. 684,482, filed Dec. 21, 1984, now abandoned.

The invention relates to a method and apparatus for guiding and collecting light which issues from a light source and which is passed as an incident primary beam to a specimen or like material to be measured, by which a measuring beam leaving the material to be measured is conducted to at least one detector or the like photoelectric receiver.

When measuring radiation outputs, the signal amplitude of the detector is directly dependent on the intensity of the light to be measured. In that procedure however, signal noise occurs, produced by the light and the detector, which, because of the random nature of the noise, rises in a sub-proportional fashion relative to the total light detected (the noise increases approximately with 1/J). Therefore, because of severe noise, very weak signals or very slight changes in a signal cannot be detected, or can only be detected with difficulty, using expensive technical equipment and long measuring integration times. It is therefore crucial for the light output of the system to be maximized in order to produce a good signal-to-noise ratio.

Very weak signals are produced primarily in the area of luminescence measuring operations. Luminescence phenomena are based on the conversion of absorbed energy into light radiation by suitable molecules. When energy is absorbed, the molecule to be observed jumps to a higher level of oscillation. The excitation energy used is generally a high-energy primary light beam, the wavelength of which differs from that of the measuring beam. Within a period of about $10^{-12}$ seconds, the excited molecule gives off a large part of the absorbed energy again by impact with the adjacent molecule. A small part of the absorbed energy can be given off again by the molecule in the form of photons in any direction, and can then be quantified by a measuring means which is capable of selectively detecting the light which is produced in that way. Generally, the degrees of intensity of the primary beam and the measuring beam differ by powers of ten.

Conventional light measuring means detect the measuring light which is irradiated in all directions only within a solid angle of a few degrees (2 to 3 degrees). The remainder of the light remains unused, and can in fact interfere with the measuring operation, in the form of stray or spurious light. Although the measuring arrangement may be of such a configuration, at high technical expense, that so-called single photon counting is made possible, such equipment is however unsuitable for routine measuring operations as it requires long measuring times and is technically exacting.

In luminometry, an increase in the intensity of the primary light does not result in a clear improvement in the measuring operation as only a small fraction of the input energy can be given off again in the form of luminescence. In contrast: high levels of intensity of primary light increase the problems of selectively detecting the secondary or measuring light as the stray or spurious light components are increased at the same time. Likewise, an unsuitable way of improving the measuring operation is to increase the concentration of luminescing molecules, as with an increasing level of concentration, the so-called concentration extinction phenomenon (saturation) becomes more and more noticeable. The more highly concentrated a solution of excited molecules is, the more frequently does an excited molecule lose all its energy by impact against adjacent molecules, before it can emit light. Therefore, it is only in respect of heavily diluted solutions and constant primary light that the level of intensity of a given fluorescence wavelength is proportional to the concentration of the fluorescing substance.

Luminescence measuring operations are primarily used nowadays in the area of clinical research and analysis. However, the methods of investigation are subject to limits by virtue of the inadequate degree of sensitivity of routine measuring equipment, as is required for measuring levels of physiological concentration in the biologically clinical area. Great efforts are being made at this time to replace radioimmunoassays (RIA) which represent a health risk from the point of view of the laboratory personnel, by fluorescence immunoassays (FIA). FIAs represent a method which is comparable to RIAs, in regard to its theoretical sensitivity but which has never achieved the expected breakthrough in the laboratory in the absence of suitable routine equipment. The present invention seeks to contribute to improving that situation.

Very weak and in particular imprecise signals also occur in absorption measuring operations in respect of media which have a strong light-scatter or diffusion effect. As conventional photometers only detect the light which passes in a straight line through the specimen or sample to be measured, and the attenuation of such light, it is often impossible to measure the actual light absorption of such media. Stray or scatter light problems occur in absorption measuring operations in respect of colloid-like substances such as photographic emulsions, solutions with macromolecules or polymers, or oily liquids.

Having regard to those considerations, the inventor set himself the aim of providing a method and an apparatus of the kind set forth in the opening part of this specification, while avoiding known disadvantages; the method and apparatus are intended to quantitatively optimize the guiding and focussing or collection of light, without a loss in respect of qualitative measuring options.

The object of the present invention is achieved in that the material to be measured is disposed at a focal point of a reflection surface which is formed at least as half an ellipsoid of revolution or paraboloid of revolution, and beams leaving said material to be measured are reflected at the reflection surface, wherein the primary beam is radiated directly in the center of the material to be measured or is passed in a straight line therethrough.

The apparatus according to the invention is distinguished in that at least the material to be measured is surrounded by a reflection surface in the form at least of a half ellipsoid of revolution and the material to be measured is disposed at the focus thereof.

The invention, further important details and features of which are to be found in the claims, is in principle based on the consideration that the incident measuring beam of the intensity $I_0$ is brought into the focal point of the reflective ellipsoid, or forms which are approximate thereto, by means of light conductors or guides or optical focussing methods, and there passes through the material to be measured. The detector or a suitable member for collecting light is disposed at the other focal point of the ellipsoid of revolution where virtually 100% of the light which issues from the specimen or sample again can be collected. That gives a major improvement in comparison with conventional light guide means, as long as the aim is to detect the secondary radiation from the sample or specimen, in as quantitative fashion as possible. If however the measuring light is to be subjected to qualitative spectral analysis, the fact that the light impinges on the focal point $F_2$ virtually from all directions in space gives rise to problems in measurement.

According to the present invention these problems are solved with the aid of associated systems of reflection paraboloids. One of the paraboloids has a central annular cut out through which the parallelized measuring light can pass in order to be determined quantitatively or made available to spectral analysis. These associated parabolic reflectors parallelize or focus the measuring light on an aperture angle which can be selected, as mentioned above, without using lens systems so that the problem of chromatic aberration can be avoided.

The invention relates primarily to all photometric means which measure luminescence phenomena, such as for example phosphorescence, fluorescence, liquid scintillation counting, wherein the measuring means makes it possible simultaneously to provide for fluorescence emissions with very high output, diffusion and absorption of the excitation light and spectral analysis of the emitted fluorescence light.

The most efficient and at the same time simplest improvement in measurement in the area of luminometry can only be achieved by an improved light guide and collection system. For that purpose, the invention has three improvements over conventional luminometers:

(a) by virtue of the possibility of radiating the primary light directly in the center of the material to be measured, a marked reduction in inherent absorption of the excitation energy is achieved;

(b) due to the rotational-elliptical light collecting system, the light output of the measuring light is improved by a factor of 50 to 100; and (c) due to the annular reflection paraboloid with focus at F2, for the first time conventional qualitative measuring options are combined with optimum quantitative light output.

A further use of the invention lies in nephelometric analysis. As is well known nephelometric analysis is a method of quantitative analysis of solutions of turbid substances by means of measurement in respect of the intensity of the scatter light (tyndallimetry) or by means of measurement of apparent extinction (turbidimetric analysis). The present invention makes it possible for the first time for both measurements to be performed simultaneously as a routine step, in order to check off the values in comparison with each other. In the area of scatter light measurement moreover, a marked improvement in the measuring operation is achieved by virtue of detecting all the scatter or stray light. In that way, it is possible better to measure slight scatter phenomena or changes in scatter factor of solid, liquid or gaseous substances and mixtures thereof or transitional forms such as for example emulsions, variations in scatter factor of cell structures or components thereof in culture solutions or the variations in scatter factor in the growth of bacteria and yeasts. For the purposes of nephelometric analysis, the present invention is modified in the following fashion: the incident measuring beam is passed in a straight line (90° with respect to the longitudinal axis) through the ellipsoid of revolution, only interrupted at the focus by the specimen or sample chamber. The light which is not scattered or diffused by the sample or specimen is measured in a straight line opposite the point of entry, while the diffused light is measured by means of a detector at the second focus of the ellipsoid of revolution.

The present invention can also be used for photochemical applications. It is known that many chemical reactions can be triggered off by light. In that connection, the molecules of the reacting substance must absorb one or more photons, under defined conditions. In the present case, the light is radiated at the one focus of the ellipsoid of rotation by means of light guides or by introducing a lamp. At the oppositely disposed focus, the material to be measured or the reaction material is exposed, in a defined amount, to irradiation on all sides, by means of a static arrangement or dynamically by means of flow cells, for a defined period of time.

The invention therefore provides a novel light guide means for use throughout the photometry art, that is to say for example for:

(a) fluorescence measuring operations;

(b) diffraction measuring operations and nephelometric analysis;

(c) absorption measuring operations;

(d) any luminescence measuring operations;

(e) kinetic measuring operations in use as in (a) to (d);

(f) liquid scintillation counting;

(g) photochemical processes; and (h) lens free parallelization or focussing with high space angle component of light from light-emitting measuring probes or any other light.

The light, modulated or unmodulated, is introduced directly into the interior of the material to be measured, for example by:

simple, multiple, modified light guides,
lens focussing,
mirror focussing.

The light collecting system according to the invention in photometry uses provides that, after passing through the material to be measured, the light is completely or partially collected, making use of virtually the full solid angle (approximately 4 Pi), the collecting system surrounding the specimen or sample in three dimensions, in the form for example of:

(1) an ellipsoid of revolution;

(2) a paraboloid of revolution;

(3) a light guide cone;

in approximate or partial configuration.

The invention also provides novel detectors for elliptical light collecting systems, which, in spherical, cubic or approximately or partially spherical or cubic form, are disposed at the focus of the possibly half ellipsoid of revolution. At that focus, for certain situations of use, it is possible to employ a light collecting member as referred to above, with light guide connected thereto, leading to the detector.

Further features, advantages and details of the invention will be apparent from the following description of preferred embodiments and with reference to the accompanying drawings which are basic diagrammatic views. In the drawings.

Figures 1, 2, 3:
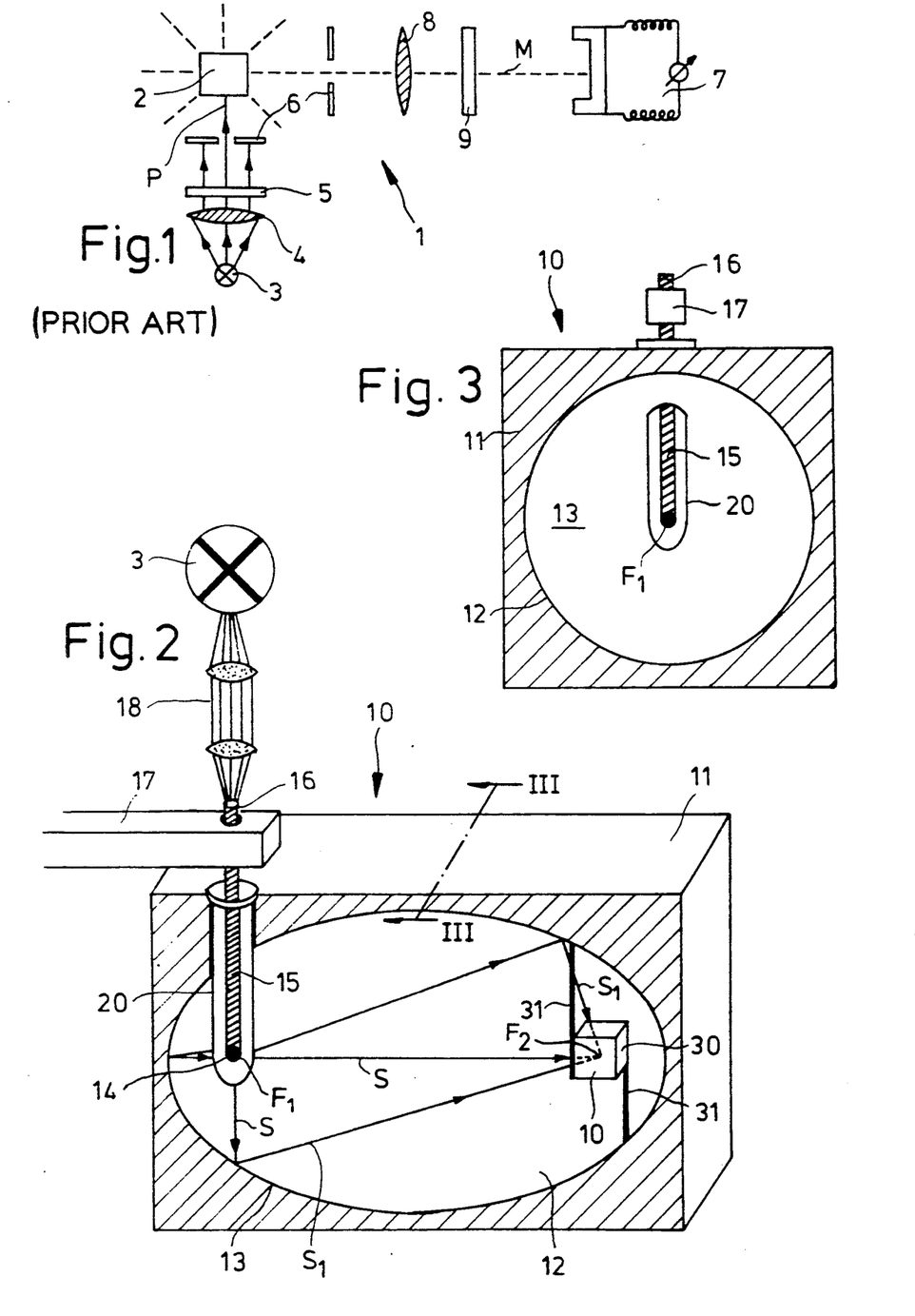
FIG. 1 shows a conventional fluorimeter.
FIG. 2 shows a perspective view of a sectioned measuring unit of a fluorescence measuring apparatus according to the invention, having a measuring chamber containing a light guide in the test tube and a detector.
FIG. 3 shows a view in cross-section through the measuring unit approximately along line III—III in FIG. 2.

In the diagrammatic view of a fluorimeter 1 as shown in FIG. 1, a sample or specimen test tube or container 2 is disposed at the point of intersection of two axes P and M. On the axis P which extends from a light source 3, being the so-called primary beam, disposed between the light source 3 and the sample test tube 2 are a lens 4 and a filter 5, and aperture members 6 on both sides of the primary beam P. The other axis which is formed by a measuring beam M terminates in a photoelectric cell 7 which also has, disposed upstream thereof, a lens 8 and a filter 9 with associated aperture members 6 disposed beside the beam.

The conventional arrangement shown in FIG. 1 is used for measuring fluorescence, which is generally interpreted as meaning fluorescence spectroscopy as a quantitative method and spectrofluorimetry as a qualitative method.

FIG. 2 shows the configuration in accordance with the invention of a first embodiment of a measuring block or unit 10 for fluorescence measuring operations. Disposed in the housing 11 thereof is a measuring chamber 12 having a reflection surface, as indicated at 13, in the form of an ellipsoid of revolution. Disposed at the left-hand focus F1 thereof is a scatter cone 14 as the end of a light guide or conductor 15.

Figure 6:
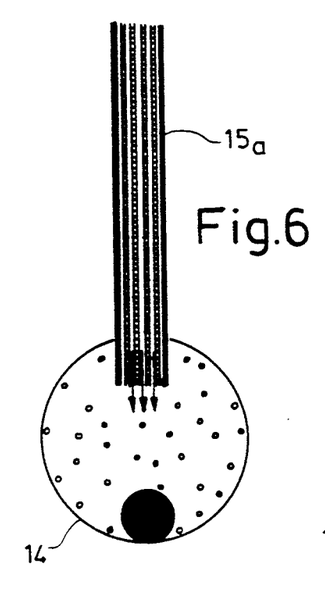
Figure 7:
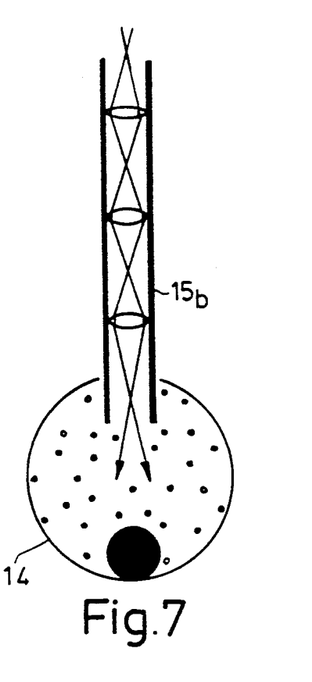

The light guide or conductor 15, being shown in FIGS. 2 through 5 as a simple light guide, in FIG. 6 as a multiple light guide 15a and in FIG. 7 as a lens focussing means 15b, is mounted outside the housing 11 with a conductor head 16 on a holding arrangement 17. From a light source 3, primary beams pass in a light guide arrangement 18 above the holding arrangement 17 to the head 16 of the light conductor 15.

Figure 4:
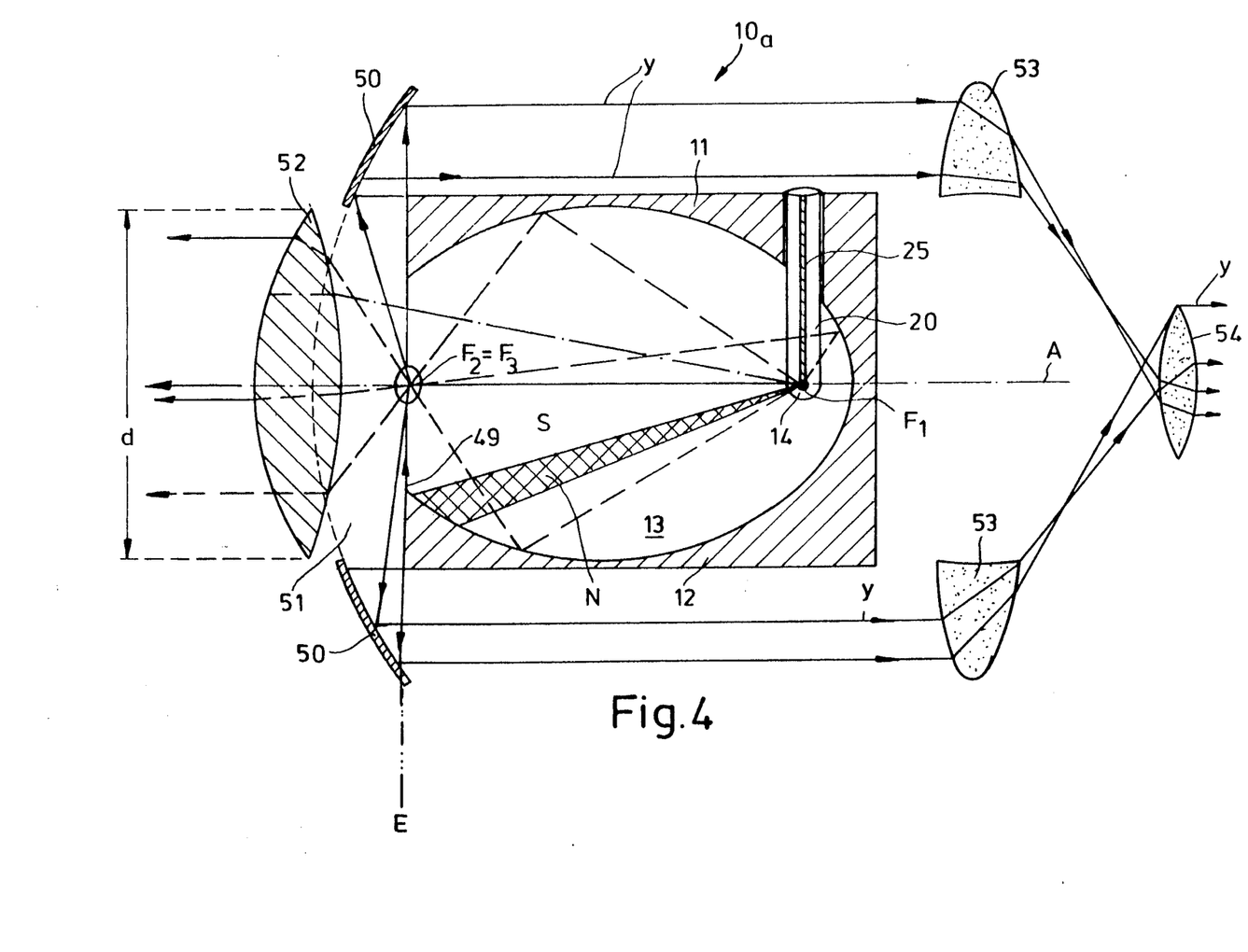
FIG. 4 shows a view in longitudinal section through another embodiment of a measuring unit having an ellipsoid of revolution which is sectioned on plane E, and an annular reflection paraboloid.
Figure 5:
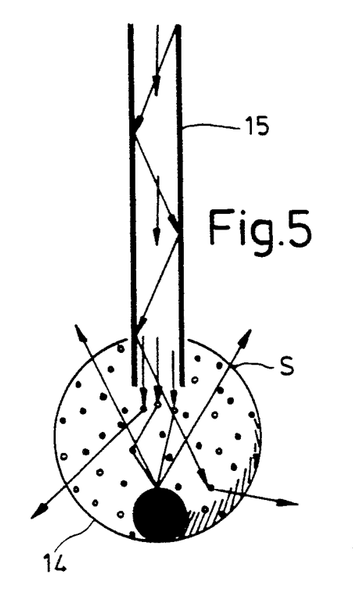
FIGS. 5 through 7 show different forms of the light guide which is shown on an enlarged scale in comparison with FIG. 2.

Within the measuring chamber 12, in FIGS. 2 through 4, the light conductor 15 with its scatter cone 14 is surrounded by a normal test tube 20.

In the embodiment shown in FIGS. 2 and 3, disposed at the other focus F2 of the measuring chamber 12 or the reflection surface 13 is a detector 30 mounted on mounting members 31. The detector 30 receives the beams S from the cone 14 both directly and also in the form of beams S1 which are reflected at the reflection surface 13.

The measuring chamber 12 of the embodiment of a measuring unit or block 10a as shown in FIG. 4 is cut at a plane E which passes through the focus F2 and which is normal to the main axis A. The resulting opening 49 in the ellipsoid of revolution for the reflection surface 13 has associated therewith, at the left-hand side in FIG. 4, an annular surface 50 in the form of a section from a reflection paraboloid, the opening 51 therein being of a diameter d which is of the length of the short axis of the ellipsoid of revolution. The focus F3 of the reflection paraboloid containing the surface 50 is at the focus F2 of the ellipsoid of revolution of the reflection surface 13.

In the embodiment shown in FIG. 4, for example a beam S extending on the main axis A passes through the annular opening 51 in the surface 50 and a convergent lens 52 to a detector (not shown), in front of which may in turn be disposed a convergent lens.

Reflected by the surface 50 are beams Y which are diverted to another convergent lens 54 by a lens system 53. From the latter, the beams Y pass in parallel mode to a monochromator which is to be envisaged as being beyond the right-hand edge of the drawing.

Reference N in FIG. 4 denotes the cross-sectional area of an annular region which is used for parallelization of the light.

Figure 8:
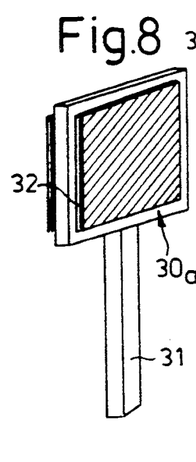
FIGS. 8 through 10 show perspective views of various embodiments of the detector.
Figure 9:
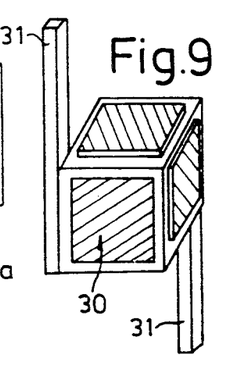
Figure 10:
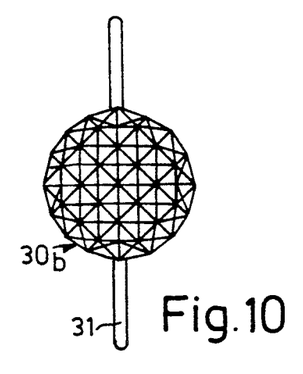

The configuration of the detector 30 may be cubic (see FIGS. 2 and 9), plate-like (see member 30a in FIG. 8) or in the form of a multi-facetted spherical member 30b as shown in FIG. 10. For certain areas of use, the detector 30 is provided with a layer or coating 32 which is partially selectively transmissive in respect of light.

Figure 11:
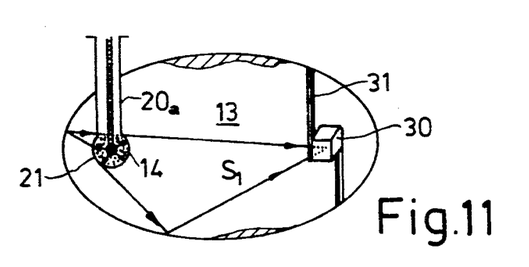
FIGS. 11 through 14 show different forms of test tube or container.
Figure 12:
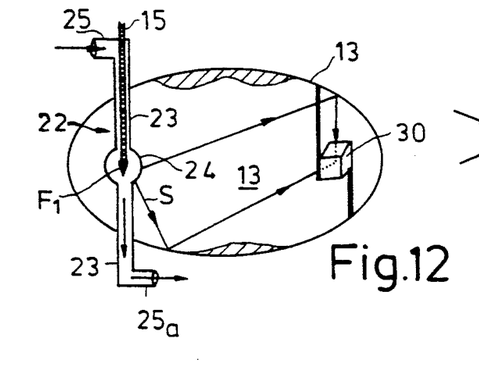

FIG. 11 shows a test tube 20a for measuring the absorption of light, with a spherical end portion 21. FIG. 12 shows a through-flow test tube 22 for the same purpose, with L-shaped tubular arms 23 which are directed coaxially with respect to each other and which open at one end into a spherical portion 24, the other ends of the arms 23 being bent over in opposite directions relative to each other and in parallel-axis relationship, to act as an inlet 25 and an outlet 25a respectively. The inlet 25 and the outlet 25a may also be interchanged with each other.

Figure 13:
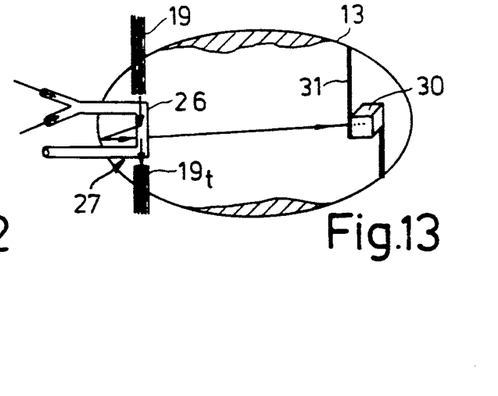

The central portion 26 of a U-shaped test tube 27 as shown in FIG. 13, being what is referred to as a 'STOP AND FLOW' test tube, for measuring kinetic phenomena, is disposed coaxially between an upper light conductor 19 and a lower light conductor 19t which provide for guiding the light in a straight line and which permit a component of the light to issue through the lower light conductor 19t.

Figure 14:
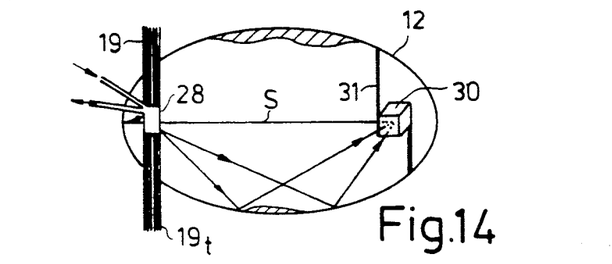

The measuring chamber 12 shown in FIG. 14 can be used for measuring scattered and unscattered light components from a sample or specimen (nephelometric analysis); a cube-like normal test tube or container 28 is disposed between two light conductors 19 and 19t, with the light being passed in a straight line through the sample or specimen to be measured.

Figure 15:
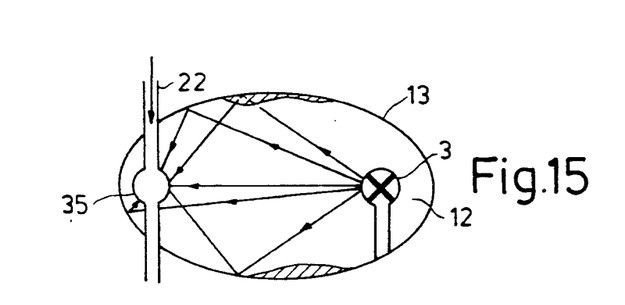
FIG. 15 shows a particular configuration of the measuring chamber for the photoactivation of chemical processes.

For the purposes of photoactivation of chemical processes, in FIG. 15, the light source 3 is disposed at a focus; disposed at the other focus is a reaction cell 35. In this case, the reaction material is continuously passed through the one focus where it is exposed on all sides to defined illumination.

Figure 16:
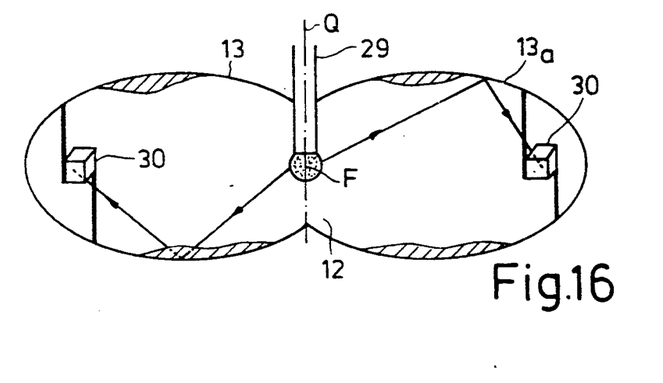
FIGS. 16 through 19 show further forms of measuring chambers.

Two ellipsoids of revolution 13 and 13a as shown in FIG. 16, which penetrate each other along a plane or line Q passing through a respective focus F have, as a joint measuring chamber 12, two detectors 30 and a liquid scintillation vial 29 at the joint focus F. That apparatus can be used to measure light flashes in liquid scintillation counting of low-energy radio isotopes. The symmetrical arrangement of the light collecting means makes it possible for light signals which are not radioactively generated to be very substantially cut out, by means of coincidence connection.

Figure 17:
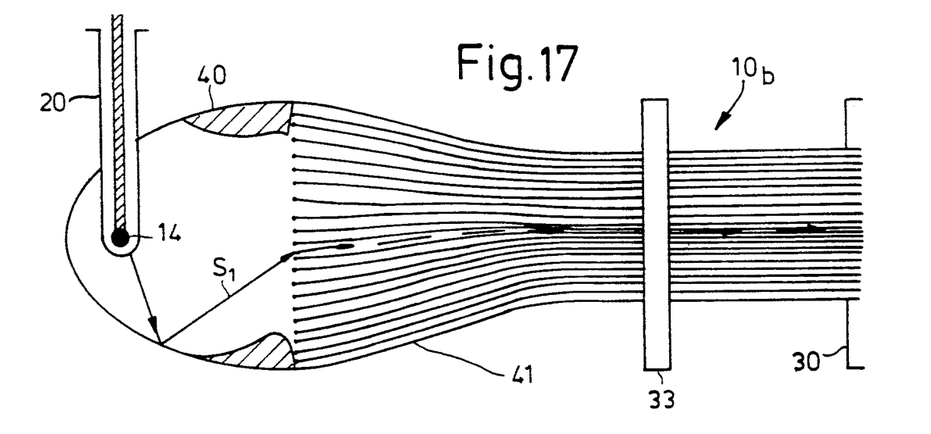

In the embodiment of the measuring unit 10b in FIG. 17, the measuring chamber 12 has a half ellipsoid of revolution 40 which is adjoined by a light conductor cone 41, in a direction towards the detector 30 with the filter 33 disposed upstream of the detector.

Figure 18:
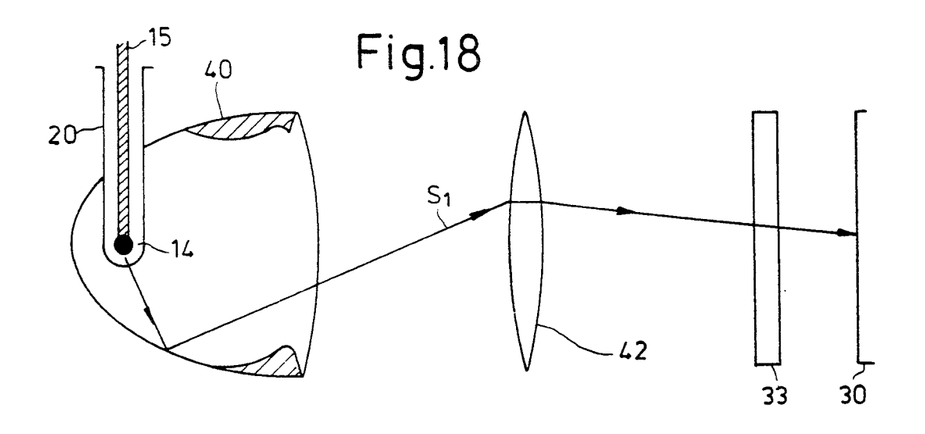

Instead of the light conductor cone 41, in FIG. 18, a convergent lens 42 is disposed downstream of the half ellipsoid of revolution 40, in the beam path S1.

Figure 19:
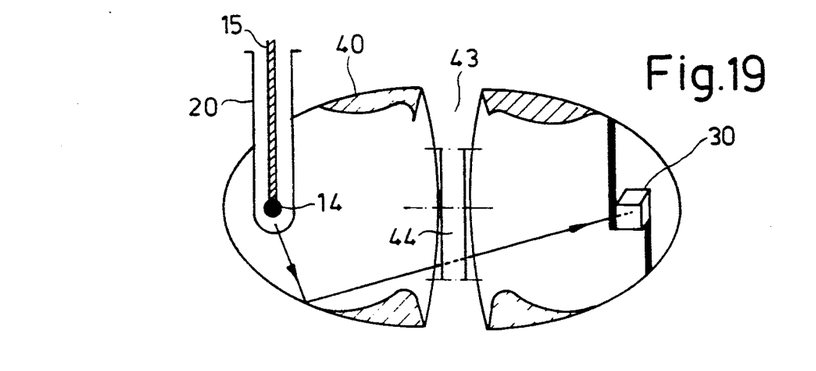

The embodiment shown in FIG. 19 comprises two half ellipsoids of revolution 40 and 40a which are disposed in coaxial relationship with each other and between which a gap 43 provides an opening for inserting filters or the like, as indicated at 44.

Figure 20:
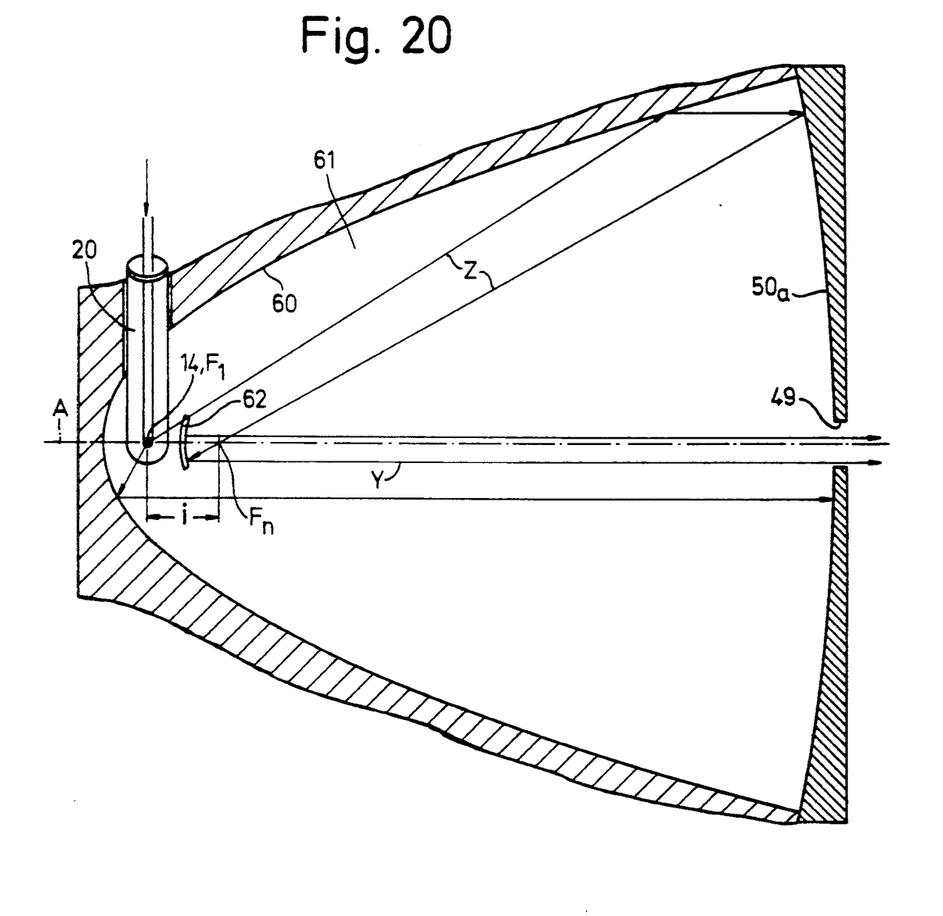
FIG. 20 shows a practical example which operates without a lens system.

The practical example according to FIG. 20, which operates without a lens system is of special importance. This figure shows a paraboloid of revolution 60 whose aperture is held by an oppositely curved parabolic reflector $50_a$, which annularly encompasses a central aperture 49 being opposed in the inner space 61 by a small full parabolic reflector 62.

At the distance i from the focal point $f_j$ of the paraboloid of revolution 60 there is located the focal point $F_n$ of the two parabolic reflectors. Rays z emitting from the bulb 20 are conducted from the paraboloid of revolution 60 to the parabolic reflector $50_a$ and from the latter reflector the the full parabolic reflector 62. The rays y get from the parabolic reflector 62 to a monochromator and after passing a prism (not shown) they get to a photodiode array, which is assumed to be on the right hand side beyond the edge of the Figure.

This system can also be used in the reverse sense of direction if it is a matter of getting very narrowly collimated light, such as laser beams, on a specimen from a space angle as large as possible.

What is claimed is:

1. A method of guiding and collecting light which comprises: providing a light source having an incident primary beam; passing the incident primary beam to a specimen to be measured fixed in position having a discrete size to provide a measuring beam leaving said specimen; conducting the measuring beam to at least one detector; providing a reflection surface of at least half an ellipsoid of revolution, said reflection surface having a first and second focus; disposing said specimen at said first focus, wherein said primary beam is radiated directly in the center of said specimen with beams leaving the specimen and passing to the second focus, whereby beams leaving said specimen are reflected at the reflection surface; providing at least two parabolic reflectors downstream of said specimen; and said method further including the step of focusing and parallelizing the beams leaving the specimen by means of said parabolic reflectors.

2. A method of guiding and collecting light which comprises:
providing a reflection surface including at least two ellipsoids of revolution which penetrate each other having a common focus and each ellipsoid having a separate second focus,
placing a specimen to be measured at the common focus, said placing step including fixing said specimen in position at said common focus; and
conducting beams leaving the specimen to at least one detector, said conducting step comprising reflecting said beams at said reflection surface and passing said beams to said separate foci.

3. A method of guiding and collecting light which comprises: providing a light source having an incident primary beam; passing the incident primary beam to a specimen to be measured fixed in position having a discrete size to provide a measuring beam leaving said specimen; conducting the measuring beam to at least one detector; providing a reflection surface of at least half an ellipsoid of revolution, said reflection surface having a first and second focus; disposing said specimen at said first focus, wherein said primary beam is radiated directly in the center of said specimen with beams leaving the specimen and passing to the second focus, whereby beams leaving said specimen are reflected at the reflection surface; and said method further including disposing the specimen in a defined amount at one of said foci, emitting light at the other focus, and irradiating the specimen on all sides for a defined period of time.

* * * * *